(12) United States Patent
Zerkowski et al.

(10) Patent No.: US 12,239,534 B2
(45) Date of Patent: *Mar. 4, 2025

(54) METHOD OF REPAIRING A DEFECTIVE HEART VALVE

(71) Applicant: HVR Cardio Oy, Espoo (FI)

(72) Inventors: Hans-Reinhard Zerkowski, Kreuzlingen (CH); Olli Keranen, Bjarred (SE); Jani Virtanen, Soderkulla (FI)

(*) Notice: Subject to any disclaimer, the term of this patent is extended or adjusted under 35 U.S.C. 154(b) by 86 days.

This patent is subject to a terminal disclaimer.

(21) Appl. No.: 18/208,323

(22) Filed: Jun. 12, 2023

(65) Prior Publication Data

US 2023/0310154 A1    Oct. 5, 2023

Related U.S. Application Data

(63) Continuation of application No. 16/810,702, filed on Mar. 5, 2020, now Pat. No. 11,696,829, which is a continuation of application No. 15/627,385, filed on Jun. 19, 2017, now Pat. No. 10,595,998.

(51) Int. Cl.
   *A61F 2/24*    (2006.01)

(52) U.S. Cl.
   CPC .......... *A61F 2/2466* (2013.01); *A61F 2/2445* (2013.01); *A61F 2210/0014* (2013.01); *A61F 2220/0008* (2013.01); *A61F 2220/0016* (2013.01); *A61F 2230/0065* (2013.01); *A61F 2230/0091* (2013.01)

(58) Field of Classification Search
   CPC ........ A61F 2/24; A61F 2/2451; A61F 2/2466; A61F 2/2445; A61F 2/2427; A61F 2/2418; A61F 2220/0016; A61F 2220/0008; A61F 2230/0091; A61F 2230/0065
   See application file for complete search history.

(56) References Cited

U.S. PATENT DOCUMENTS

| | | | |
|---|---|---|---|
| 2007/0080188 A1* | 4/2007 | Spence | A61F 2/2445 623/2.11 |
| 2007/0250161 A1* | 10/2007 | Dolan | A61F 2/2466 623/2.37 |
| 2008/0172035 A1* | 7/2008 | Starksen | A61B 17/3468 604/508 |

* cited by examiner

*Primary Examiner* — Vi X Nguyen
(74) *Attorney, Agent, or Firm* — Patent Grove AB; Tomas Friend

(57) ABSTRACT

A method of repairing a defective heart valve is disclosed comprising directing an implant delivery catheter to form a first curve of the implant delivery catheter around chordae of the heart valve on a ventricular side of the heart valve, inserting the implant delivery catheter through the heart valve to an atrial side thereof, forming a second curve of the delivery catheter along an annulus of the heart valve on the atrial side, and ejecting an annuloplasty implant from the delivery catheter while retracting the delivery catheter such that the annuloplasty implant is arranged along the first and second curve on the ventricular and atrial side.

7 Claims, 13 Drawing Sheets

METHOD OF REPAIRING A DEFECTIVE HEART VALVE

RELATED APPLICATIONS

This application is a continuation of and claims priority to U.S. Pat. No. 15,627,385 filed Jun. 19, 2017, entitled Method Of Repairing A Defective Heart Valve, which is hereby incorporated herein by reference in its entirety.

FIELD OF THE INVENTION

This invention pertains in general to the field of cardiac valve repair. More particularly the invention relates to a method of repairing a defective heart valve.

BACKGROUND OF THE INVENTION

Diseased mitral and tricuspid valves frequently need replacement or repair. The mitral and tricuspid valve leaflets or supporting chordae may degenerate and weaken or the annulus may dilate leading to valve leak. Mitral and tricuspid valve replacement and repair are frequently performed with aid of an annuloplasty ring, used to reduce the diameter of the annulus, or modify the geometry of the annulus in any other way, or aid as a generally supporting structure during the valve replacement or repair procedure. Such annuloplasty rings or other annuloplasty implants are put into position and fixated to the tissue by various implantation procedures.

It is known that cardiac valve repair is a time critical and difficult procedure. Although minimally invasive catheter-based procedures are employed today, known solutions are associated with lengthy procedures that depend heavily on the skills of the medical staff. Besides from the immediate difficulties, e.g. associated with the delivery, placement and fixation of the annuloplasty implant, the occurrence of complications arising in the long-term follow-up can not be neglected. Frequent interventions may thus be required to ensure correct functioning over time, which will also impact the recovery and health of the patient. Another problem is to ensure that a significant part of the annulus is reshaped while providing for atraumatic engagement with the anatomy.

A further problem is the cumbersome placement of annuloplasty implants due to interference from the surrounding anatomy such as the chordae of the valve leaflets. This typically results in entanglement of the implant into the chordae, and time-consuming repositioning may be required. Generally, it is a problem with previous solutions that once the implant is ejected from the delivery catheter, it is difficult to fully control position of the implant since the amount of control of the distal parts ejected is reduced.

The above problems may have dire consequences for the patient and the health care system. Patient risk is increased.

Hence, an improved method of repairing a defective heart valve would be advantageous and in particular allowing for avoiding more of the above-mentioned problems and compromises, and in particular allowing for facilitated positioning and fixation of an annuloplasty implant while reducing the time of the intervention, and providing for increased patient safety.

OBJECTS AND SUMMARY OF THE INVENTION

Accordingly, examples of the present invention preferably seeks to mitigate, alleviate or eliminate one or more deficiencies, disadvantages or issues in the art, such as the above-identified, singly or in any combination by providing a device according to the appended patent claims.

According to a first aspect a method of repairing a defective heart valve is provided comprising directing an implant delivery catheter to form a first curve of the implant delivery catheter around chordae of the heart valve on a ventricular side of the heart valve, inserting the implant delivery catheter through the heart valve to an atrial side thereof, forming a second curve of the delivery catheter along an annulus of the heart valve on the atrial side, and ejecting an annuloplasty implant from the delivery catheter while retracting the delivery catheter such that the annuloplasty implant is arranged along the first and second curve on the ventricular and atrial side.

According to a second aspect a method of repairing a defective heart valve is provided comprising inserting a flexible and removable coronary sinus contractor device into a coronary sinus (CS) adjacent said heart valve, positioning a proximal expandable portion of the coronary sinus contractor device against a tissue wall at the entrance of said CS, positioning a distal anchoring portion of the coronary sinus contractor device inside said CS, temporarily transferring said coronary sinus contractor to an activated state in which the shape of the annulus of the heart valve is modified to a modified shape to be retained by an annuloplasty implant. The method further comprising directing an implant delivery catheter to the position of the valve, delivering an annuloplasty implant from the implant delivery catheter so that the annuloplasty implant is positioned around the annulus of the valve, fixating said annuloplasty implant to retain said modified shape, and removing the coronary sinus contractor device.

Further examples of the invention are defined in the dependent claims, wherein features for the second and subsequent aspects of the disclosure are as for the first aspect mutatis mutandis.

Some examples of the disclosure provide for a facilitated positioning of an annuloplasty implant at a heart valve.

Some examples of the disclosure provide for a facilitated fixation of an annuloplasty implant at a heart valve.

Some examples of the disclosure provide for facilitating resizing the annulus of a heart valve.

Some examples of the disclosure provide for facilitating resizing the annulus of a heart valve before positioning an annuloplasty implant at the heart valve.

Some examples of the disclosure provide for a less time consuming implantation of an annuloplasty implant at a heart valve.

Some examples of the disclosure provide for improved long-term reliability of a remodeled heart valve.

Some examples of the disclosure provide for facilitated guidance of an annuloplasty implant to an annulus of a heart valve.

Some examples of the disclosure provide for a more secure implantation of an annuloplasty implant in narrow anatomies.

Some examples of the disclosure provide for increased steerability or maneuverability of an annuloplasty implant.

Some examples of the disclosure provide for increased accuracy in positioning an annuloplasty implant at the annulus and thereby reducing the risk of complications.

Some examples of the disclosure provide for a reduced risk of damaging the surrounding tissue or the annuloplasty implant valve during an implantation procedure.

Some examples of the disclosure provide for better ability to reposition an annuloplasty implant.

Some examples of the disclosure provide for avoiding interference of the annuloplasty implant with the chordae of the valve leaflets.

Some examples of the disclosure provide for improved control of the position of the implant when being delivered from a delivery device.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1A:
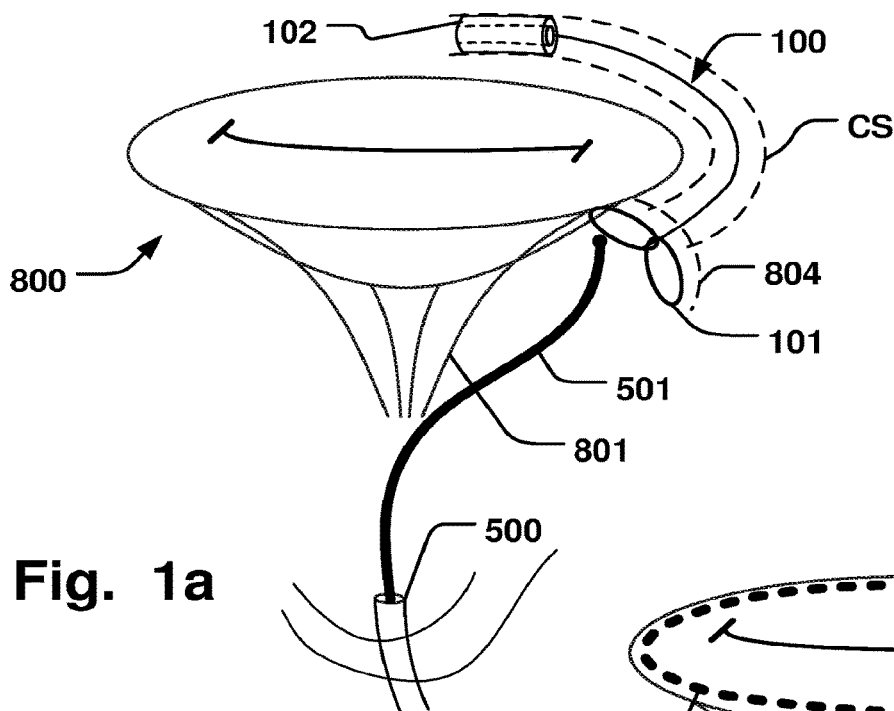
FIG. 1a is a schematic illustration of an arrangement of a delivery device and a coronary sinus downsizing device in a method according to one example.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on examples applicable to cardiac valve implants such as annuloplasty rings. However, it will be appreciated that the invention is not limited to this application but may be applied to many other annuloplasty implants and cardiac valve implants including for example replacement valves, and other medical implantable devices.

Figure 1B:
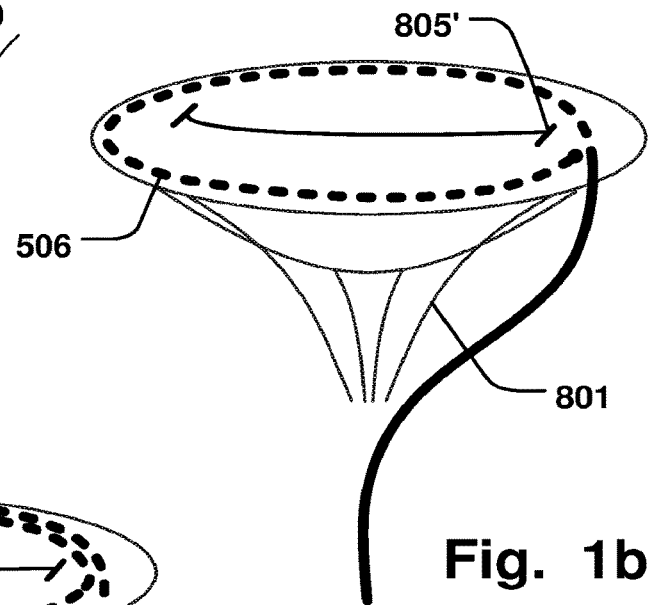
FIG. 1b is a schematic illustration of an arrangement of a delivery device in a method according to one example, where the delivery device has been further advanced to form a first curve around chordae of the heart.
Figure 1C:
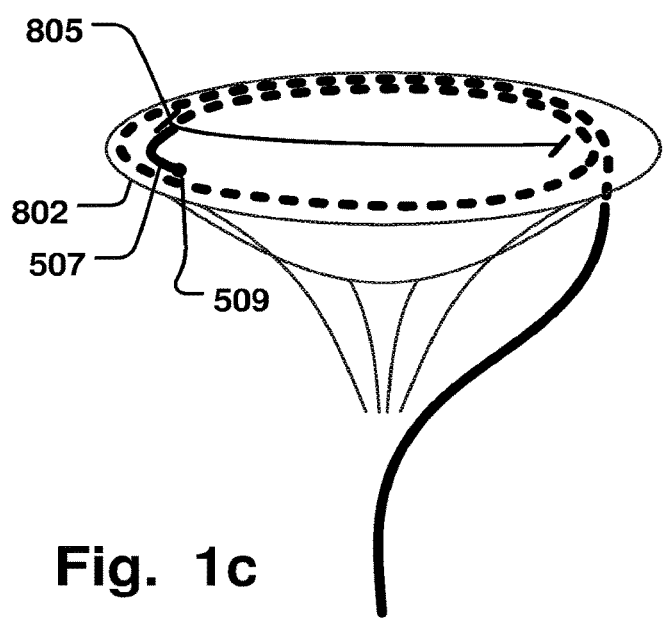
FIG. 1c is a schematic illustration of an arrangement of a delivery device in a method according to one example, where the delivery device has been further advanced to begin forming a second curve on an atrial side of the heart valve.
Figure 1D:
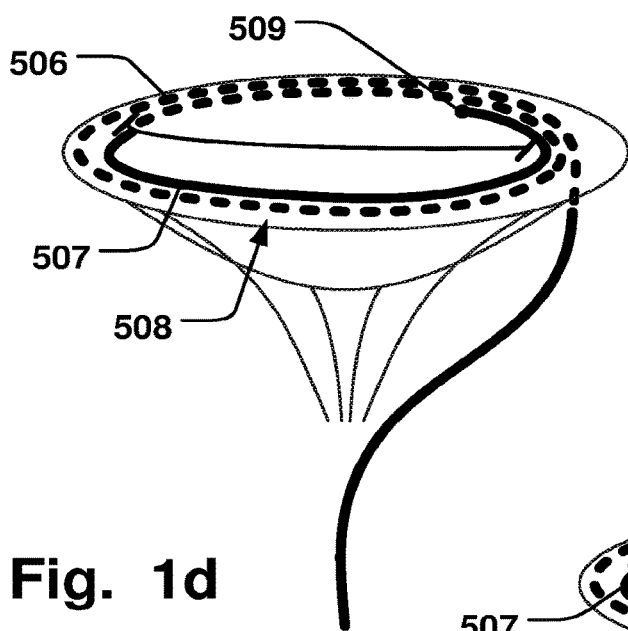
FIG. 1d is a schematic illustration of an arrangement of a delivery device in a method according to one example, where the delivery device has been further advanced to form a second curve along the annulus of the heart valve.
Figure 1E:
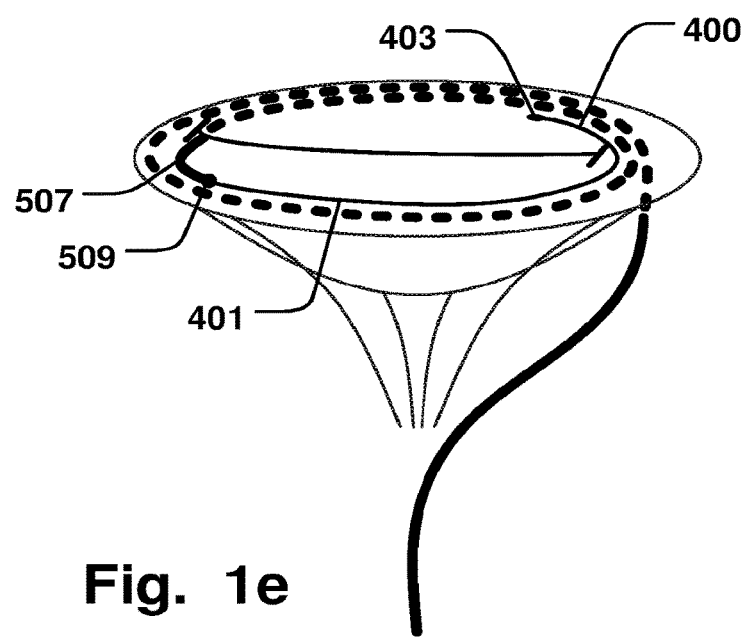
FIG. 1e is a schematic illustration of an arrangement of a delivery device in a method according to one example, where an annuloplasty implant has been ejected on the atrial side while retracting the delivery device.
Figure 1F:
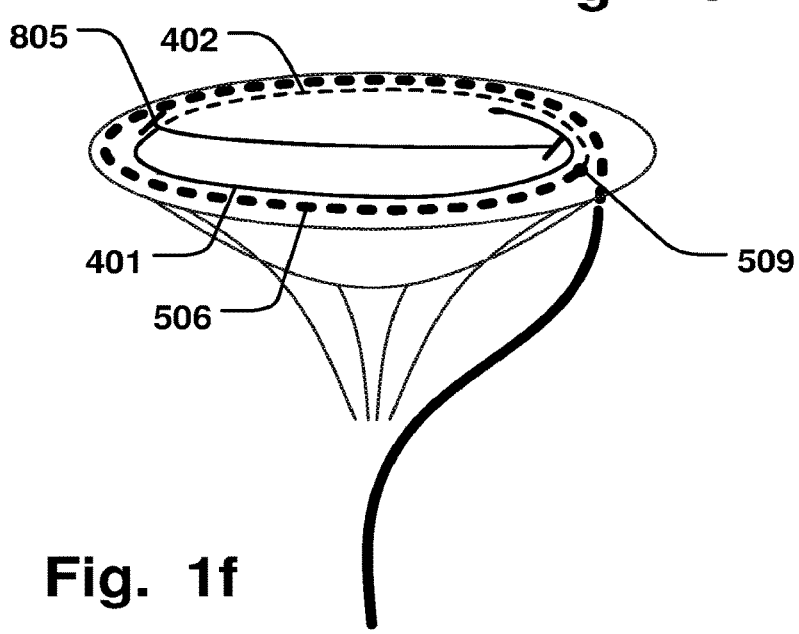
FIG. 1f is a schematic illustration of an arrangement of a delivery device in a method according to one example, where the delivery device has been further retracted and the annuloplasty implant contacts the heart valve on the atrial and ventricular side thereof.
Figure 1G:
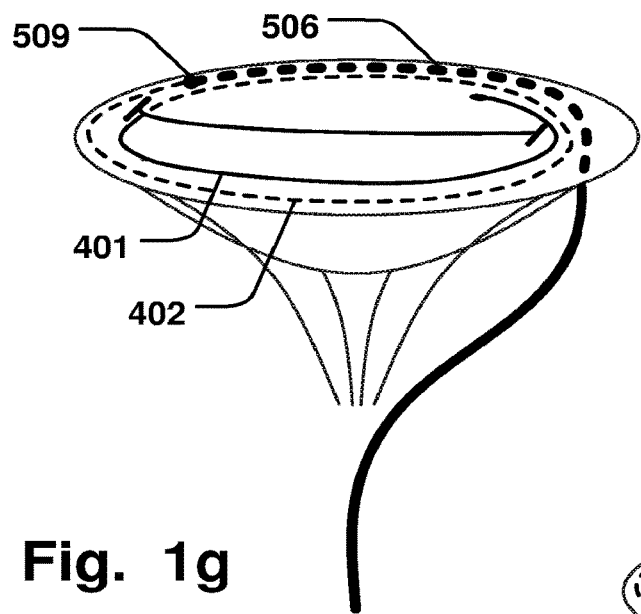
FIG. 1g is a schematic illustration of an arrangement of a delivery device in a method according to one example, where the delivery device has been further retracted.
Figure 1H:
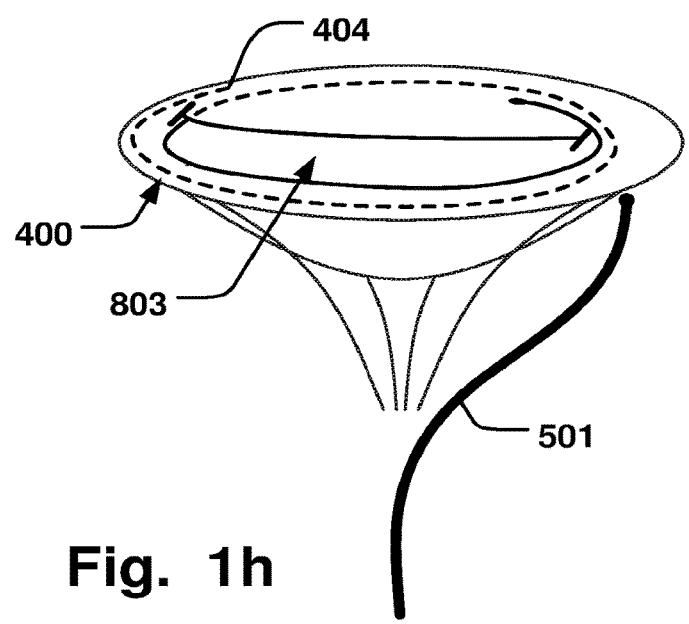
FIG. 1h is a schematic illustration of an arrangement of a delivery device in a method according to one example, where the annuloplasty implant contacts the heart valve on the atrial and ventricular side thereof in a helix-shaped configuration.
Figure 8:
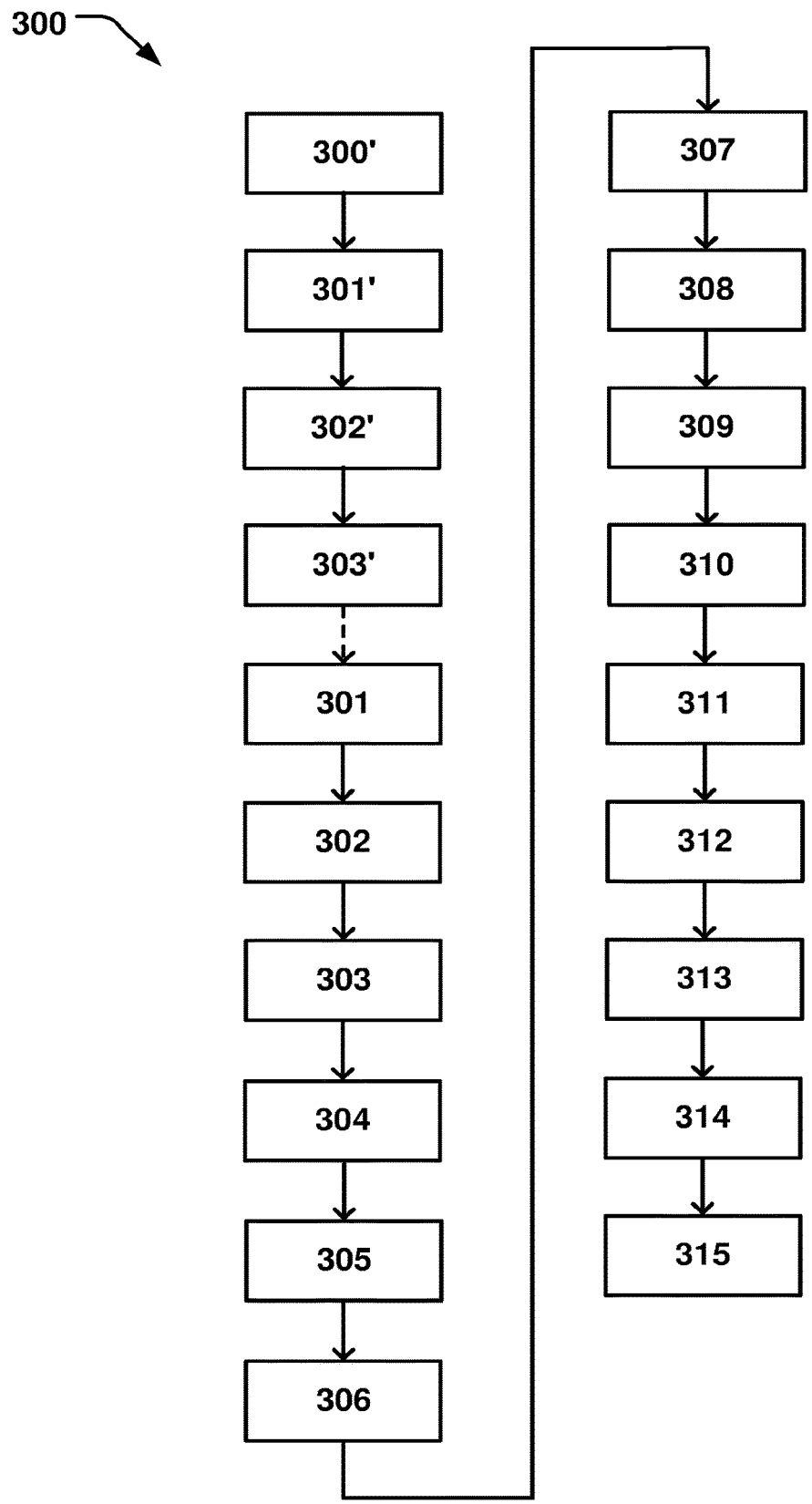
FIG. 8 is a flow-chart of a method of repairing a defective heart valve according to one example.

A method 300 of repairing a defective heart valve 800 is disclosed. The method 300 is schematically illustrated in FIG. 8, in conjunction with FIGS. 1a-i. The order in which the steps are described should not be construed as limiting, and it is conceivable that the order of the steps may be varied depending on the particular procedure. As shown in FIGS. 1a-b, the method 300 comprises directing 302 an implant delivery catheter 501 to form 303 a first curve 506 of the implant delivery catheter 501 around the chordae 801 of the heart valve on a ventricular side of the heart valve 800. The heart valve may be the mitral valve, and the ventricle may thus be the left ventricle. The method 300 may comprise positioning the delivery catheter 501 in the ventricle by accessing 301 the ventricle through the apex of the heart with an introducer 500. The delivery catheter 501 may then then be inserted through the introducer 500, as illustrated in the example of FIG. 1a. Alternatively, the method 300 may comprise positioning the delivery catheter 501 in the ventricle by accessing the ventricle through the aortic valve, or by creating access to the left ventricle through the septum between the right and left ventricle. Regardless, the method 300 comprises forming 303 a first curve 506 of the implant delivery catheter 501 around the chordae 801 of the heart valve on a ventricular side of the heart valve 800. The delivery catheter 501 may thus be first navigated to the ventricular space between the chordae 801 and the heart muscle, so that the delivery catheter 501 can be curved around the chordae 801 on the ventricular side. The method 300 comprises inserting 305 the implant delivery catheter 501 through the heart valve 800 to the atrial side thereof, and forming 307 a second curve 507 of the delivery catheter 501 along an annulus 802 of the heart valve 800 on the atrial side, which is illustrated in FIGS. 1c-d. The delivery catheter 501 may be advanced such that annulus is followed in a counter-clockwise direction. In the example of FIG. 1c, the delivery catheter 501 has begun to be inserted through the heart valve 800 to form the second curve 507 on the atrial side. Parts of the delivery catheter 501 on the ventricular side has been illustrated with dashed lines for clarity of presentation. In FIG. 1d, the delivery catheter 501 has been further advanced through the valve 800, taking e.g. the distal tip 509 of the delivery catheter 501 as a reference point. The method 300 comprises ejecting 309 an annuloplasty implant 400 from the delivery catheter 501 while retracting 310 the delivery catheter 501 such that the annuloplasty implant 400 is arranged along the first and second curve 506, 507, on the ventricular and atrial side of the valve. FIG. 1e illustrates an example where the implant 400 has been ejected and the delivery catheter 501 has been retracted on the atrial side, along part of the second curve 507, e.g. again comparing the position of the distal tip 509 in FIGS. 1d-e. The implant 400 is thus abutting the valve tissue on the atrial side. In the example of FIGS. 1d-e, the implant 400 has begun to be ejected when the distal tip 509 of the delivery catheter 501 has reached the position illustrated in FIG. 1d, while simultaneously retracting the delivery catheter 501. The position of a distal tip 403 of the implant 400 in this example thus corresponds substantially to the previous position of the distal tip 509 of the delivery catheter 501. Since the delivery catheter 501 is simultaneously retracted along the curvature of the first and second curve 506, 507, when ejecting the implant 400, the positioning of the implant 400 will effectively correspond to withdrawing the delivery catheter as a sheath previously covering the implant 400 which already is arranged along the curvature provided by the delivery catheter 501 when forming the first and second curve 506, 507, thereof. Hence, the delivery catheter 501 can effectively serve as a guide for the implant 400 for the positioning thereof on the ventricular and atrial side, without having to navigate the implant 400 into the correct position after being ajected from the delivery catheter 501. This provides for improving the control of the positioning of the implant 400, since otherwise, as soon as an implant is ejected from a delivery catheter, the amount of control and steerability on the ejected part is diminished by the decoupling from the physical constrain of the catheter. Positioning the implant 400 as described above removes the steerability requirement on the implant 400 after being ejected, due to the guiding of the implant 400 to the final position, while being fully confined within the delivery catheter 501. This also minimizes the risk of interference with the surrounding anatomy, such as entanglement of the implant 400 with the chordae 801. A more reliable and secure positioning of the implant 400 at the heart valve 800 is thus achieved. FIGS. 1f-g illustrate a further retraction of the delivery catheter 501, i.e. the distal tip 509 thereof is again positioned on the ventricular side. The implant 400 is thus in contact with the valve tissue on both the atrial and ventricular side. As with the delivery catheter 501, the parts of the implant 400 positioned on the ventricular side are illustrated with dashed lines for clarity of presentation. In FIG. 1h the delivery catheter 501 has been fully retracted from the valve 800. In the example shown in FIGS. 1g-h, the implant 400 has been decoupled from the delivery catheter 501 when the distal tip 509 thereof reach the position illustrated in FIG. 1g, thus substantially corresponding to the position of a proximal end 404 of the implant 400.

Forming the first curve 506 of the delivery catheter 501 may comprise forming 304 a loop of the delivery catheter around the chordae 801, as illustrated in FIGS. 1b-c. A majority of, or substantially all of the chordae may be circumflexed by the first curve 506 of the delivery catheter 501. Inserting the implant delivery catheter 501 through the heart valve 800 may comprise inserting 306 the implant delivery catheter through a first commissure 805 of the heart valve 800, as schematically illustrated in FIG. 1c. The first curve 506 and the second curve 507 may form a helix shape 508 as further illustrated in e.g. FIG. 1d. The first and second curve 506, 507, may thus form two continuously connected loops, on opposite sides of the heart valve, being connected through the commissure 805. This provides for achieving an efficient deployment of an annuloplasty implant 400 around the annulus of the valve 800, on both the ventricular and atrial sides. Before being looped around the chordae 801, the delivery catheter 501 may be navigated to a position adjacent to a second commissure 805' of the heart valve 800, opposite the first commissure 805 through which the implant 400 is inserted from the ventricular to the atrial side. The first and second commissures 805, 805', may correspond to the anterior and posterior commissures of the mitral valve, respectively.

The annuloplasty implant 400 may have a predefined ring-shape having a curvature corresponding substantially to the first and second curve 506, 507, such that, when ejected from the delivery catheter 501, the annuloplasty implant 400 is arranged along the first and second curve 506, 507. By having a predefined ring-shape approximating the curvature of the first and second curves 506, 507, of the delivery catheter 501, the annuloplasty implant 400 may be readily aligned around the heart valve 800 along the extension of the first and second curves 506, 507, when the implant 400 is ejected and the delivery catheter is simultaneously withdrawn, with a minimum of movement of the implant 400 relative to the valve 800 when the delivery catheter 501 is withdrawn. A more stable and controlled positioning of the implant 400 along the annulus of the heart valve 800 may thus be achieved. The predefined ring-shape of the implant 400 can be determined for example by a heat treatment procedure during manufacturing of the implant 400. When the implant is confined in the delivery catheter 501, it assumes an elongated configuration, until it is ejected, whereby it assumes the predefined shape, i.e. the relaxed shape of the shape-memory of the material from which the ring is formed.

The predefined ring-shape may be a helix-shaped ring, whereby a first support ring 401 of the helix-shaped ring is positioned on the atrial side and a second support ring 402 of the helix-shaped ring is positioned on the opposite ventricular side when ejecting the annuloplasty implant 400 from the delivery catheter 501 while retracting the delivery catheter 501, as illustrated in e.g. FIGS. 1e-h, with the gradual withdrawal of the delivery catheter 501. The leaflets 803 of the valve 800 can thereby be pinched between the first and second support rings 401, 402, providing for a stable fixation of the implant 400 at the heart valve 800. Arranging the delivery catheter 501 to form a helix-shaped configuration of the first and second curves 506, 507, on the ventricular and atrial side is thus particularly advantageous for deployment of a helix-shaped implant 400, and provides for a facilitated and improved fixation of a helix-shaped annuloplasty implant 400 at the heart valve 800. It is conceivable however that the delivery catheter 501 may be arranged to form differently shaped curves 506, 507, on the ventricular and/or atrial side of the valve 800, and that the shape of the annuloplasty implant 400 may be varied accordingly. For example, the angle by which the first and/or second curve 506, 507, spans the periphery of the heart valve may be increased or decreased depending on the corresponding length of the implant 400.

The method 300 may comprise aligning 308 the first and second curve 506, 507, of the delivery catheter 501 generally in the plane of the heart valve 800 such that the annuloplasty implant 400 is positioned generally in said plane when retracting the delivery catheter 501. Aligning the delivery catheter 501 substantially in the plane of the valve 800, i.e the plane in which the leaflets of the valve extends, provides for a facilitated positioning of the annuloplasty implant 400, with a minimum of repositioning required until the implant 400 extends along the annulus 802 of the valve 800. The curvature of the delivery catheter 501 may be adapted by passive or active manipulation thereof. In the former case, the delivery catheter 501 may be formed of a shape-memory material that assumes a predefined shape when releasing a radial compression force thereon, such as by pushing the delivery catheter 501 from the introducer 500 or a separate sheath. Active manipulation may be provided by actuating steering mechanisms of the delivery catheter 501.

The method 300 may comprise inserting 300' a flexible and removable coronary sinus contractor device 100 (CS device) into a coronary sinus vessel (CS) adjacent the heart valve 800. Inserting the CS device may comprise positioning 301' a proximal expandable portion 101 of the CS device against a tissue wall 804 at the entrance of the CS, positioning 302' a distal anchoring portion 102 of the CS device inside the CS, and temporarily transferring 303' the CS device to an activated state in which the shape of the annulus 802 is modified to a modified shape to be retained by the annuloplasty implant 400. The method 300 may further comprise fixating 311' the annuloplasty implant 400 to retain said modified shape, and removing 315' the CS device 100. The CS device is schematically illustrated in FIG. 1a, and is also described in further detail below. FIGS. 1b-l does not include the CS device 100 for clarity of presentation. The shape of the annulus 802 may thus be temporarily modified while fixating the annuloplasty implant 400, so that the desired modified shape can be fixated by the annuloplasty implant 400. The method 300 thus provides for an efficient downsizing of the annulus 802, so that the leaflets 803 of the heart valve 800 may coapt as intended, while the new shape of the annulus 802 can be reliably maintained by the improved delivery and control of the annuloplasty implant 400 as elucidated above.

Figure 1I:
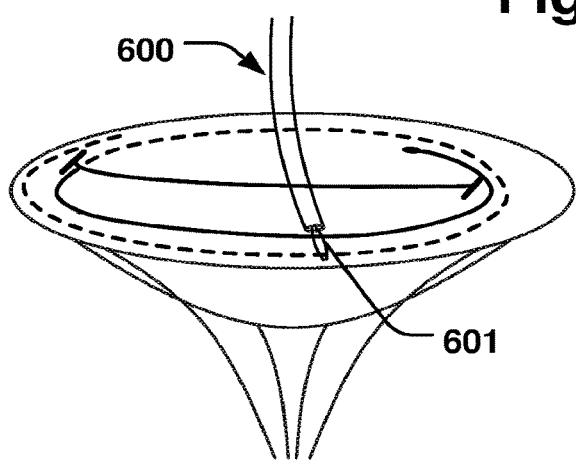
FIG. 1i is a schematic illustration of an arrangement of a delivery device in a method according to one example, where the annuloplasty implant is fixated by a fastening device.

Fixating the annuloplasty implant 400 to retain said modified shape may comprise placing 312' fastening units 601 on the annuloplasty implant 400 from a fastening device 600. The fastening device 600 may be delivered 313' to the atrial side of the valve 800, as illustrated in FIG. 1i or the fastening device 600 may be delivered 314 to the ventricular side of the valve 800, via e.g. a transapical access, or access via the aortic valve or through the septum. The fastening units 601 may be sutures, clips, screws, barbs, or other structures configured to fixate the position of the tissue relative to the implant 400, so that the modified shape of the annulus can be maintained when the CS device 100 is removed. It is further conceivable that the fastening units 601 are integrated into the implant 400 and subsequently activated to be ejected from the implant 400 to pierce the tissue, and fixate the implant 400 to the tissue.

Figure 2A:
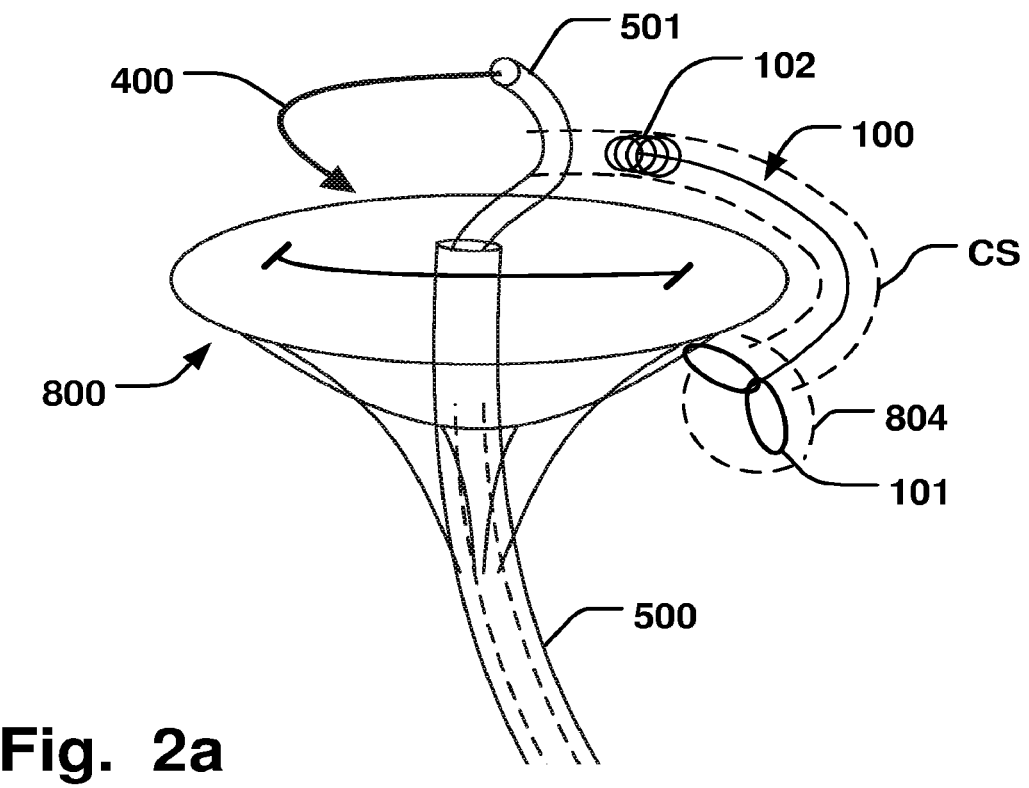
FIG. 2a is a schematic illustration of an arrangement of a delivery device, an annuloplasty implant and a coronary sinus downsizing device in a method according to one example.
Figure 2B:
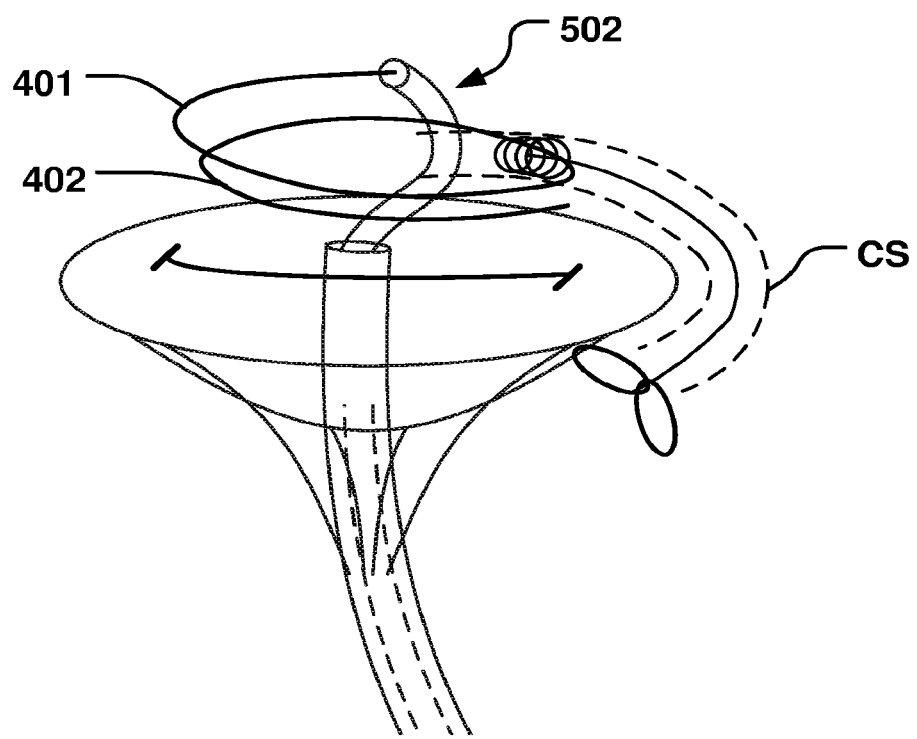
FIG. 2b is a schematic illustration of an arrangement of a delivery device, an annuloplasty implant and a coronary sinus downsizing device in a method according to one example, where the annuloplasty implant has been further ejected from the delivery device.
Figure 3A:
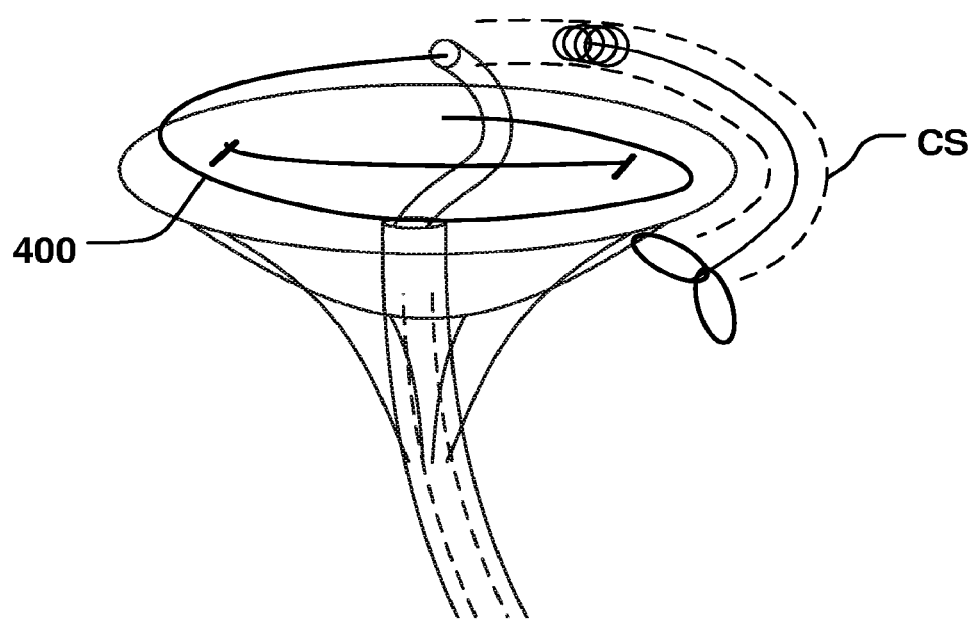
FIG. 3a is a schematic illustration of an arrangement of a delivery device, an annuloplasty implant and a coronary sinus downsizing device in a method according to one example.
Figure 7:
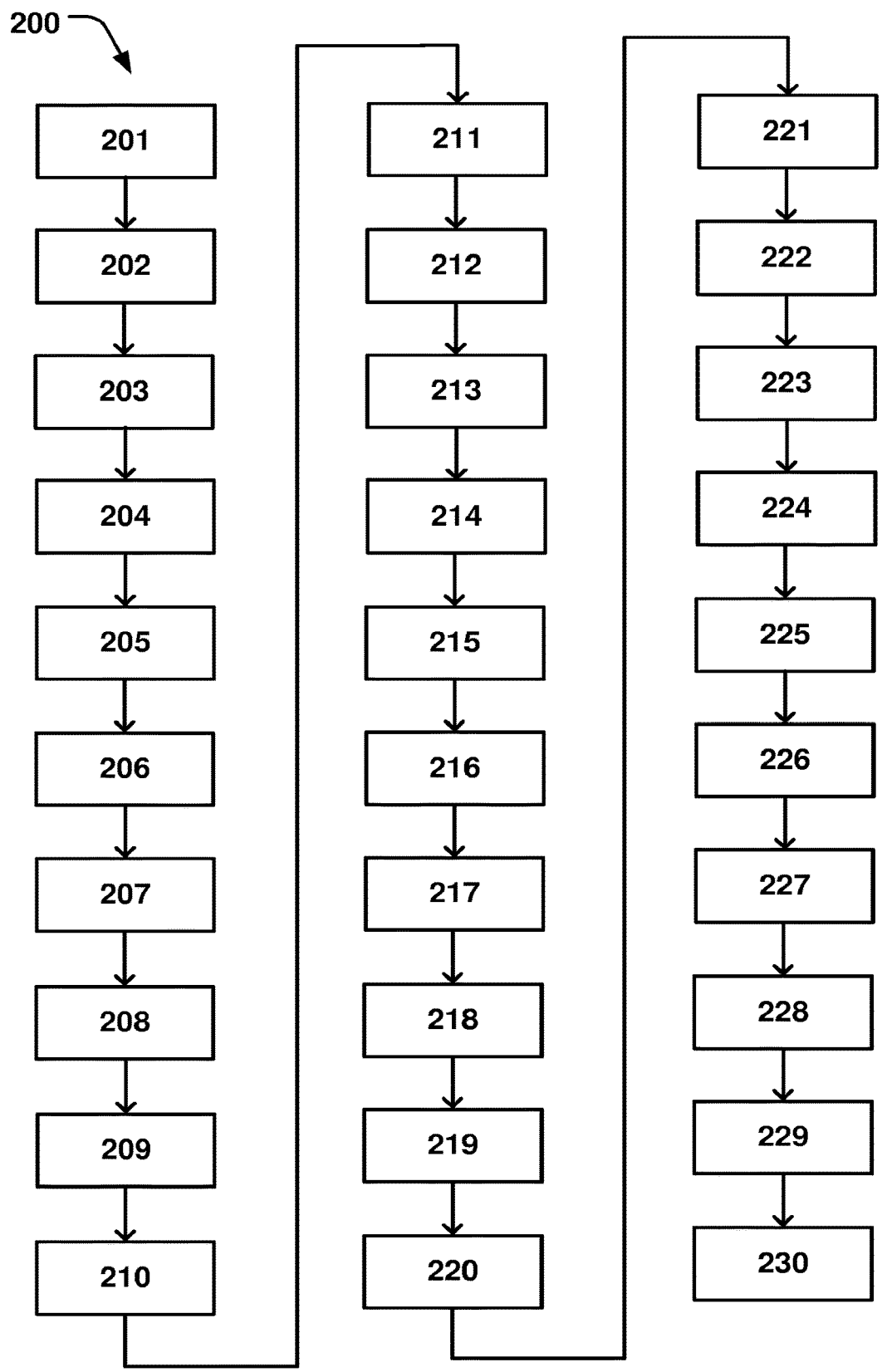
FIG. 7 is a flow-chart of a method of repairing a defective heart valve according to one example.

A further method 200 of repairing a defective heart valve 800 is disclosed. The method 200 is schematically illustrated in FIG. 7. The order in which the steps are described should not be construed as limiting, and it is conceivable that the order of the steps may be varied depending on the particular procedure. The method 200 comprises inserting 201 a flexible and removable coronary sinus contractor device 100 (CS device) into the coronary sinus vessel (CS) adjacent the heart valve 800. Inserting the CS device comprises positioning 202 a proximal expandable portion 101 of the CS device against a tissue wall 804 at the entrance of the CS, positioning 203 a distal anchoring portion 102 of the CS device inside the CS, and temporarily transferring 204 the CS device to an activated state in which the shape of the annulus 802 of the heart valve is modified to a modified shape to be retained by an annuloplasty implant 400. The method 200 further comprises directing 206 an implant delivery catheter 501 to the position of the valve from the ventricular side of the valve, and delivering 207 an annuloplasty implant 400 from the implant delivery catheter 501 so that the annuloplasty implant 400 is positioned around the annulus of the valve. Positioning the delivery catheter 501 at the valve from the ventricular side should be construed as first positioning the delivery catheter 501 in the ventricle of the heart and then positioning the delivery catheter 501 at the valve. The heart valve may be the mitral valve, and the ventricle may thus be the left ventricle. The method 200 may comprise positioning the delivery catheter 501 in the ventricle by accessing 205 the ventricle through the apex of the heart with an introducer 500. The delivery catheter 501 may then then be inserted through the introducer 500, as illustrated in the example of FIG. 2*a*. Alternatively, the method 200 may comprise positioning the delivery catheter 501 in the ventricle by accessing the ventricle through the aortic valve, or by creating access to the left ventricle through the septum between the right and left ventricle. The method 200 further comprises fixating 208 the annuloplasty implant 400 to retain said modified shape, and removing the CS device 100. FIG. 2*a* schematically illustrates the CS device 100 inserted into the CS, and the proximal expandable portion 101 thereof positioned at the tissue wall 804 at the entrance of the CS. The distal anchoring portion 102 is anchored inside the CS, distally of the proximal expandable portion 101. The CS device 100 is then transferred to an activated state where the shape of the CS vessel is modified. Since the CS lies adjacent the mitral valve and follows a curvature around the annulus of the mitral valve, the annulus of the mitral valve is also modified. In this manner the annulus may be downsized, i.e. retracted to assume a smaller cross-section, and/or a reduced diameter, and/or assume an increased radius of curvature, such that the previously dilated leaflets of the valve may be brought closer together, i.e. co-apt, to restore the function of the valve. FIG. 2*a* illustrates a distal end of the introducer 500 being positioned adjacent the heart valve 800, such as the mitral valve. The implant delivery catheter 501 has been pushed out of a distal opening of the introducer 500, and is thereby arranged in the atrium of the heart, adjacent the valve 800. The implant 400 has been partly ejected from the implant delivery catheter 501 in FIG. 2*a*. Turning to FIG. 2*b*, the implant 400 has been further ejected and assumes, in this example, a coil- or helix-shaped configuration with a first support ring 401 and a second support ring 402, as explained in further detail below. The implant 400 is positioned around the annulus as seen in FIGS. 1*c-d*. In this example, the first- and second support rings are positioned on either side of the valve 800, but it is conceivable that the implant 400 may assumes a variety of shapes, such as a single-loop ring which is continuous, i.e. closed loop, such as D-shaped, or has two free ends, i.e. discontinuous, such as C-shaped. FIG. 3*a* illustrates an example where the implant 400 has a single ring configuration. FIGS. 1*d-e* schematically illustrate fixating the implant 400 by a fastening device 600, as explained further below. The implant 400 retains the modified shape of the annulus, such that the leaflets co-apt, and the temporarily fixated CS device can be removed, as well as the implant delivery catheter 501, the introducer 500, and the fastening device 600. It is thus provided for an efficient and reliable procedure to fixate an annuloplasty implant 400 at the annulus of the heart, thanks to the efficient combination of ventricular access and delivery of the implant 400 from the ventricular side, and the annulus modification procedure via the CS vessel. This combination allows for example improved visibility from the trial side of the valve, since the annulus modification is provided for by the CS device which is in the CS vessel, and the implant 400 is delivered from the ventricular side. This may then advantageously provide for improved control of the entire implantation procedure, due to the enhanced view from the atrial side. The combination of having a re-shaping procedure from the CS and an annuloplasty implant 400 delivered from the ventricular side thus provides for an efficient synergy also due to the fact that it's possible to provide for the maximum benefit from the efficient downsizing procedure of the annulus by the CS device because of the facilitated delivery and positioning of the implant 400 via the ventricular access. The improved control and reliability of the procedure also provides for enhancing the adaptability of the procedure to varying anatomies of the heart and the heart valve 800, e.g. such as particularly narrow or otherwise abnormal anatomies that would otherwise be impossible due treat.

Delivering the annuloplasty implant 400 from the implant delivery catheter 501 may thus comprise ejecting 209 the annuloplasty implant 400 from the delivery catheter 501 whereby it assumes a predefined ring-shape above the heart valve 800 in the atrium of the heart. The predefined ring-shape of the implant 400 can be determined for example by a heat treatment procedure during manufacturing of the implant 400. When the ring is confined in the delivery catheter 501, it assumes an elongated configuration, until it is ejected, whereby it assumes the predefined shape, i.e. the relaxed shape of the shape-memory of the material from which the ring is formed.

Figure 2C:
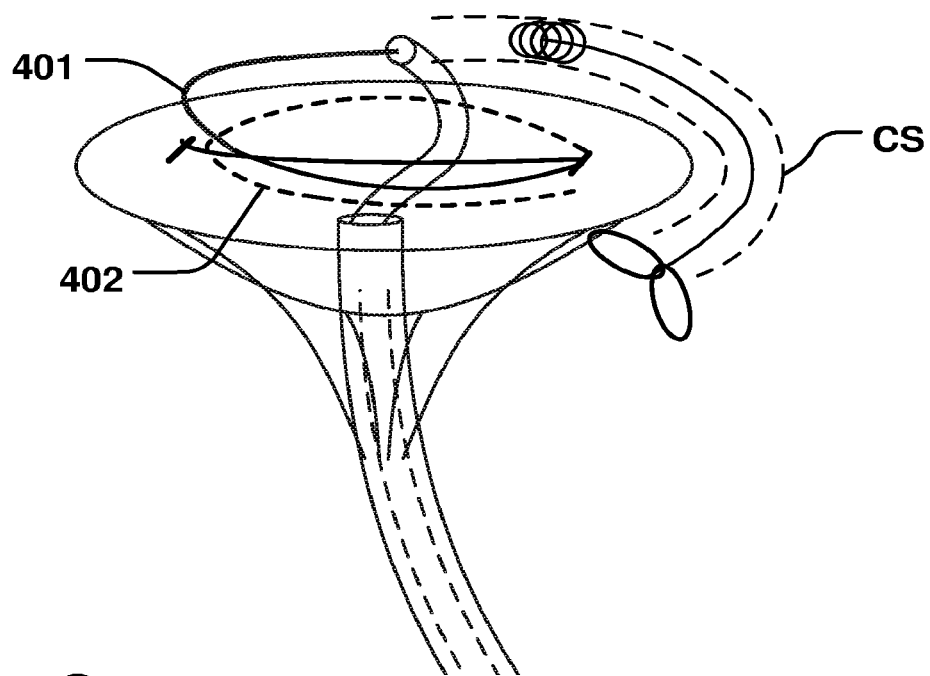
FIG. 2c is a schematic illustration of an arrangement of a delivery device, an annuloplasty implant and a coronary sinus downsizing device in a method according to one example, where the annuloplasty implant has been partly arranged through a commissure of the heart valve.

As mentioned in relation to FIGS. 1*b-e*, the predefined ring-shape may be a helix-shaped ring. The method 200 may comprise rotating and retracting 210 the delivery catheter 501 such that the helix-shaped ring is rotated through the valve 800 and a first support ring 401 of the helix-shaped ring is positioned on an atrial side of the valve 800 and a second support ring 402 is positioned on the opposite ventricular side of the valve 800. The leaflets 803 of the valve 800 can thereby be pinched between the first and second support rings 401, 402. FIG. 2*b* illustrate the first- and second rings 401, 402, positioned in the atrium, whereas in FIG. 2*c* the delivery catheter 501 has been rotated and retracted such that the free end of the second support ring 402 has been inserted in the commissure of the valve 800 and subsequently further rotated so that approximately the entire second support ring 402 is positioned on the ventricular side of the valve 800. The shape of the annulus which has been modified by the CS device 100 can thus be efficiently retained by the pinching effect between the first and second support rings 401, 402. FIGS. 4*b-c* illustrate another example where the first and second support rings 401, 402, are rotated into place on opposite sides of the valve 800, in this case around rotational axis 503' of the delivery catheter 501.

The method 200 may comprise aligning 211 a curvature of a distal portion 502 of the delivery catheter 501 such that the annuloplasty implant 400 is positioned generally in the plane of the valve 800 when ejected from the delivery catheter 501. FIG. 2*b* illustrates a curvature of the distal portion 502 of the delivery catheter 501 that is aligned so that the ring-shaped implant 400 is ejected with a desired angle in relation to the plane in which the valve 800 extends. This provides for facilitating insertion of the implant 400 into the valve 800 so that the first and second rings 401, 402, are positioned on either side of the valve leaflets. Also in the case of having a single-ring implant 400, as illustrated in FIG. 3*a*, having a determined curvature, such as aligned approximately in the plane of the valve 800, will facilitate positioning of the implant 400 around the annulus. The curvature of the distal portion 502 may be adapted to depending on the particular procedure, the size of the surrounding anatomy, and on the shape of the implant 400. The curvature may be adapted by passive or active manipulation of the distal portion 502. In the former case, the distal portion 502 may be formed of a shape-memory material that assumes a predefined shape when releasing a radial compression force thereon, such as by pushing the distal portion 502 out from the introducer 500 or a separate sheath. Active manipulation may be provided by actuating steering mechanisms of the delivery catheter 501.

Figure 4A:
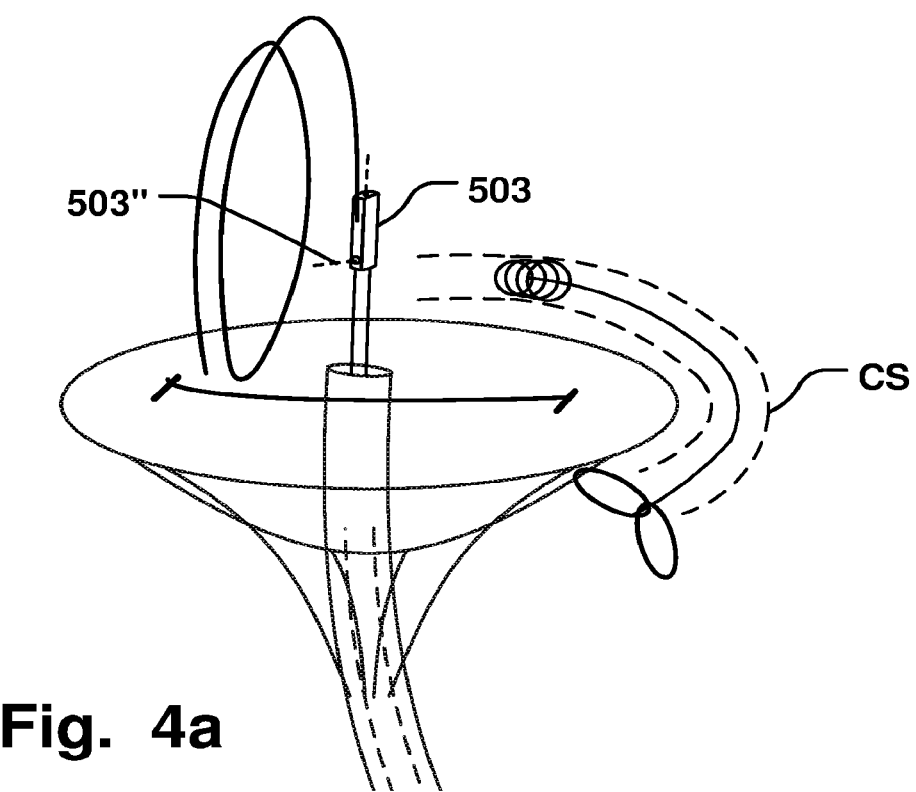
FIG. 4a is a schematic illustration of an arrangement of a delivery device, an annuloplasty implant and a coronary sinus downsizing device in a method according to one example.
Figure 4B:
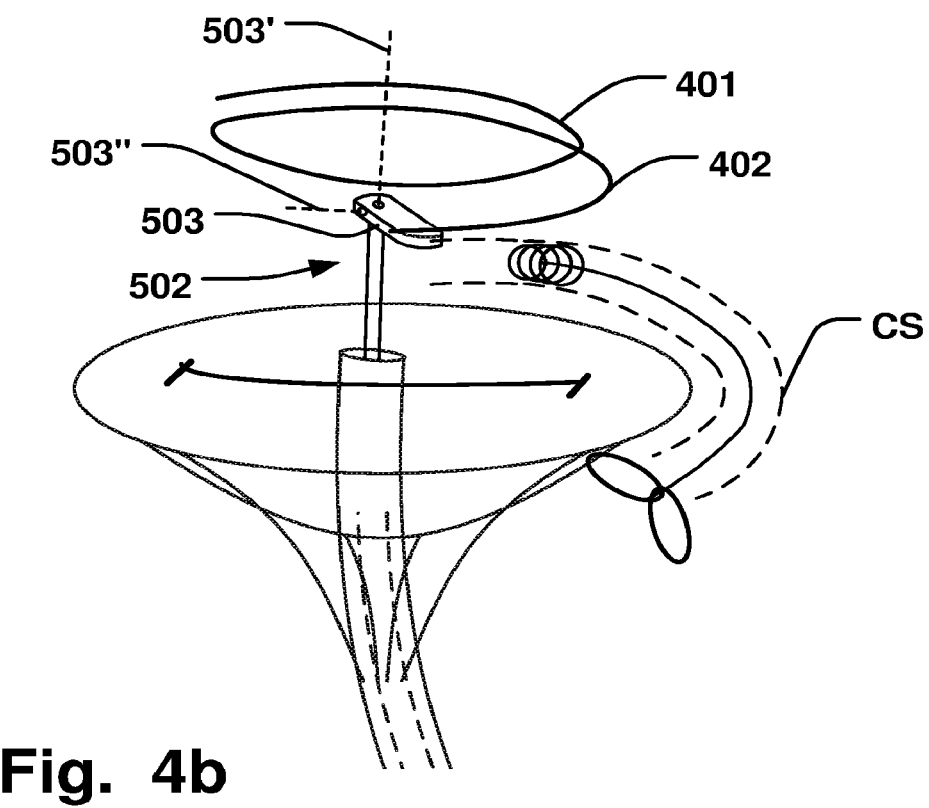
FIG. 4b is a schematic illustration of an arrangement of a delivery device, an annuloplasty implant and a coronary sinus downsizing device in a method according to one example, where the annuloplasty implant has been rotated in the atrium of the heart.
Figure 4C:
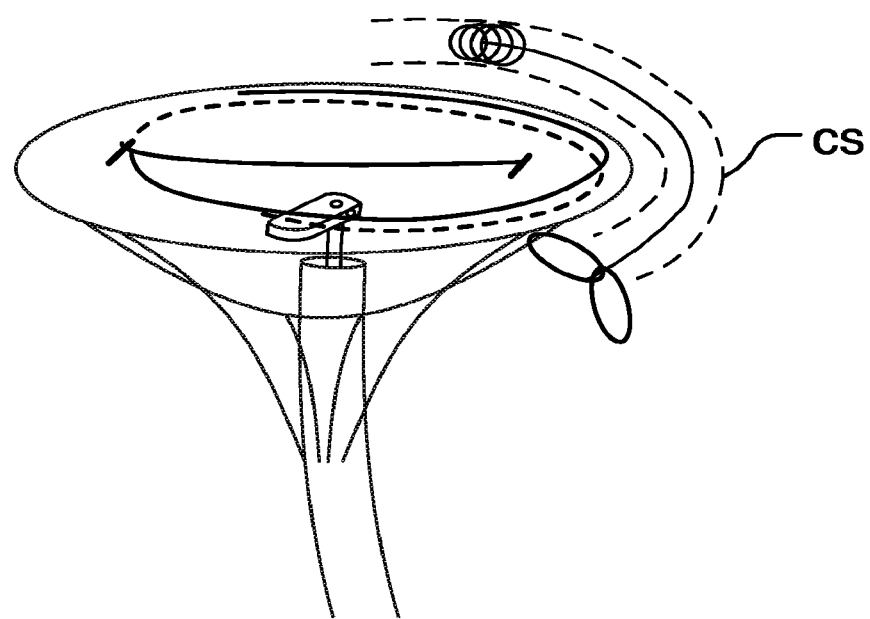
FIG. 4c is a schematic illustration of an arrangement of a delivery device, an annuloplasty implant and a coronary sinus downsizing device in a method according to one example, where the annuloplasty implant has been positioned on the ventricular- and atrial sides of the heart valve.

The method 200 may comprise rotating 212 the annuloplasty implant 400 in the atrium, after being ejected from the delivery catheter 501, by pivoting an actuator 503 at a distal portion 502 of the delivery catheter 501, to align the annuloplasty implant 400 generally in the plane of the valve 800, as illustrated in FIGS. 4a-b. When first ejecting the implant 400 in the atrium, it may assume a configuration as illustrated in FIG. 4a. I.e. the implant 400 assumes a ring-shape that spans a plane which forms an angle with the plane in which the valve 800 extends, e.g. such an approximately perpendicular angle, as illustrated in FIG. 4a. In this case the implant 400 is helix-shaped, but it is also conceivable that the implant 400 may assume any other shape such as single-loop D- or C-shape, as described above. The actuator 503 may thus pivot around rotational axis 503" to adjust the angle of the implant 400 relative the plane of the valve 800. In FIG. 4b, the implant 400 has been pivoted so that the plane in which the implant extends is approximately parallel with the plane of the valve 800. This provides for facilitating delivery of the implant 400 into the atrium, i.e. since it can be ejected from the delivery catheter 501 in the longitudinal direction of the catheter, as seen in FIG. 4a, while being subsequently pivoted to facilitate the positioning at the annulus. And in the case of having a helix-shaped implant, the first and second support rings 401, 402, may be rotated further into place as illustrated in FIG. 4c, by rotation around the longitudinal axis 503' of the delivery catheter 501. Rotational axis 503" may thus be substantially perpendicular to the longitudinal axis 503'. Thus, the implantation of the implant 400 at the annulus is facilitated by the added degree of control provided.

Although the examples discussed above describe ejection of the implant in the atrium of the heart, it is conceivable that the method 200 may comprise ejecting 213 the annuloplasty implant 400 from the delivery catheter 501 in the ventricle of the heart, and positioning 214 the annuloplasty implant 400 at the valve 800 from a ventricular side of the valve 800. The delivery catheter 501 may thus be positioned below the valve 800, in the ventricle, and a helix-shaped implant 400 may be ejected through one of the commissures so that the first support ring 401 is positioned on the atrial side, and the second support ring is positioned on the ventricular side.

Figure 2D:
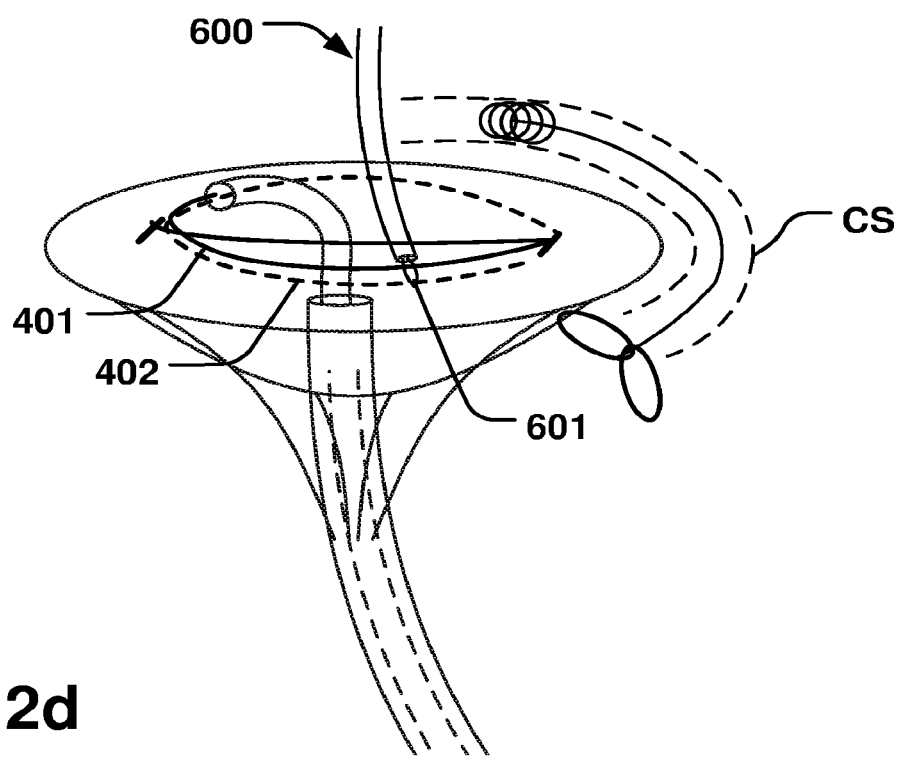
FIG. 2d is a schematic illustration of an arrangement of a delivery device, an annuloplasty implant, a coronary sinus downsizing device, and a fastening device in a method according to one example, where fastening units are placed on the annuloplasty implant.
Figure 2E:
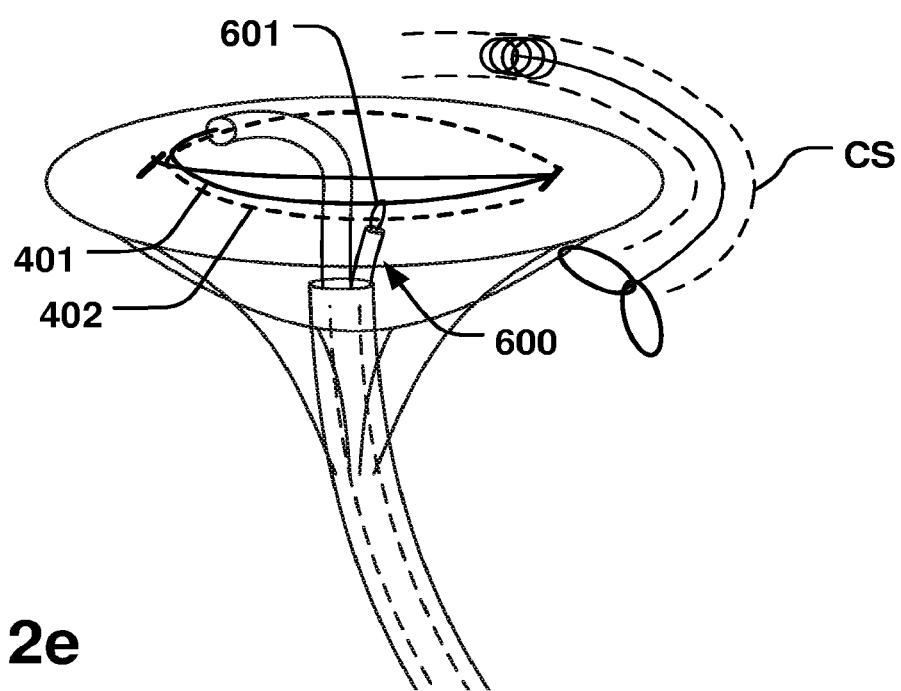
FIG. 2e is a schematic illustration of an arrangement of a delivery device, an annuloplasty implant, a coronary sinus downsizing device, and a fastening device in a method according to one example, where fastening units are placed on the annuloplasty implant.

Fixating the annuloplasty implant 400 to retain the modified shape provided by the CS device 100 may comprise placing 215 fastening units 601 on the annuloplasty implant 400 from a fastening device 600. The fastening device 600 may be delivered 216 to the atrial side of the valve 800, as illustrated in FIG. 2d, or the fastening device 600 may be delivered 217 to the ventricular side of the valve 800, as illustrated in FIG. 2e, via e.g. a transapical access, or access via the aortic valve or through the septum. The fastening units 601 may be sutures, clips, screws, barbs, or other structures configured to fixate the position of the tissue relative to the implant 400, so that the modified shape of the annulus can be maintained when the CS device is removed. It is further conceivable that the fastening units 601 are integrated into the implant 400 and subsequently activated to be ejected from the implant 400 to pierce the tissue, and fixate the implant 400 to the tissue.

Figure 6:
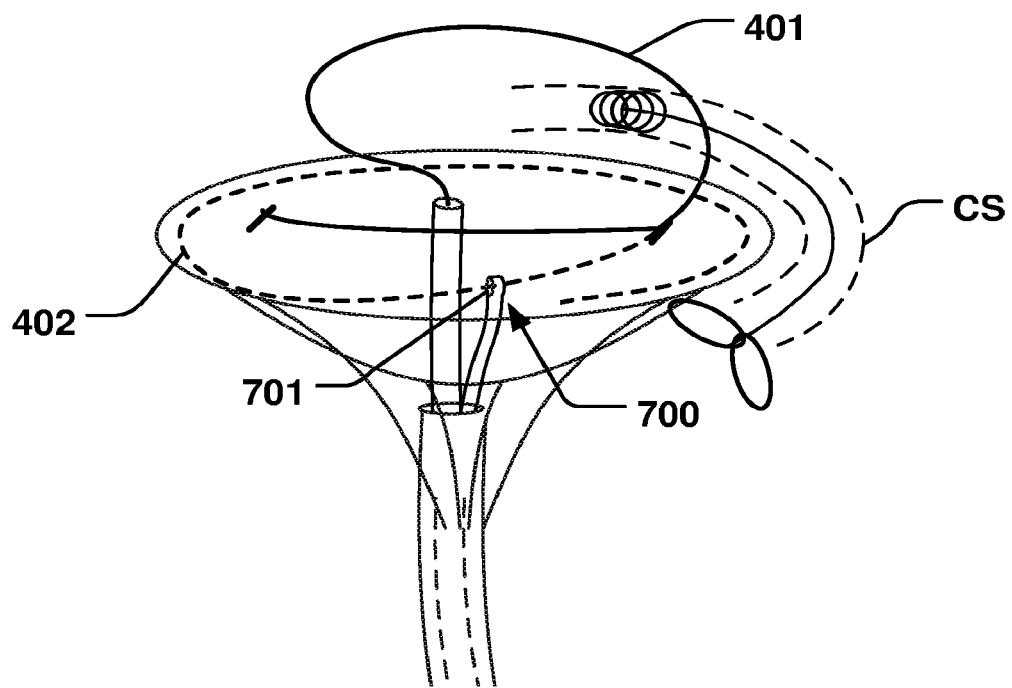
FIG. 6 is a schematic illustration of an arrangement of a delivery device, an annuloplasty implant, a coronary sinus downsizing device, and a stabilizing unit in a method according to one example.

The method 200 may comprise guiding 218 the annuloplasty implant 400 with a stabilizing unit 700 arranged in apposition with the annuloplasty implant 400 while positioning the annuloplasty implant 400 at the annulus of the heart valve 800, as schematically illustrated in FIGS. 3 and 6. This may advantageously provide for increased control of the implantation procedure, to make the implantation more reliable and/or completed in less amount of time. The stabilization unit 700 may thus be configured to guide the implant 400 by exerting a correcting force against the implant 400 while positioning the latter at the annulus. The correcting force may be a pulling, pushing, or torqueing force, that directs the implant 400 in a desired direction.

Figure 3B:
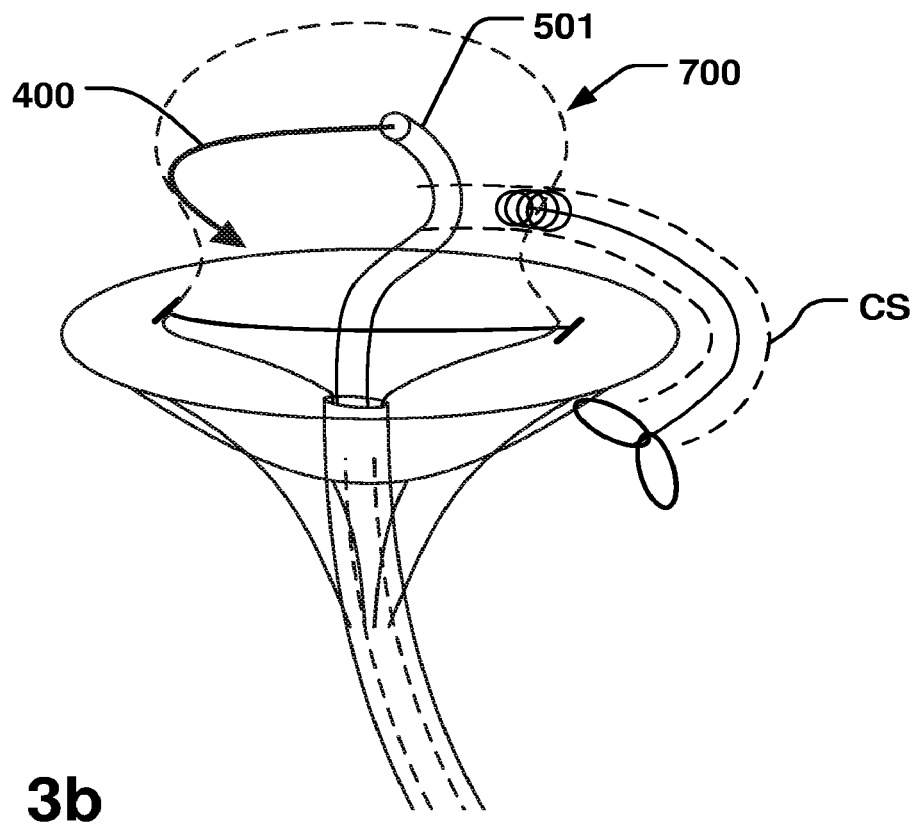
FIG. 3b is a schematic illustration of an arrangement of a delivery device, an annuloplasty implant, a coronary sinus downsizing device, and a stabilizing unit in a method according to one example.

The stabilizing unit 700 may be positioned 219 at the commissures of the heart and extending at least partly into the atrium of the heart, as illustrated in FIG. 3b. Placing the stabilizing unit 700 at the commissures efficiently anchors the stabilizing unit 700 into position, so that a reliable guiding of the implant 400 can be achieved. By extending in to the atrium, the stabilizing unit 700 can be arranged to guide the implant 400 while it is ejected into the atrium from the delivery catheter 501 as illustrated in FIG. 3b. The stabilizing unit 700 may comprise further guiding elements configure to slide against the implant 400 such as wires forming apertures or C-shaped elements that engage the implant 400 (not shown) to facilitate the guiding.

Figure 5A:
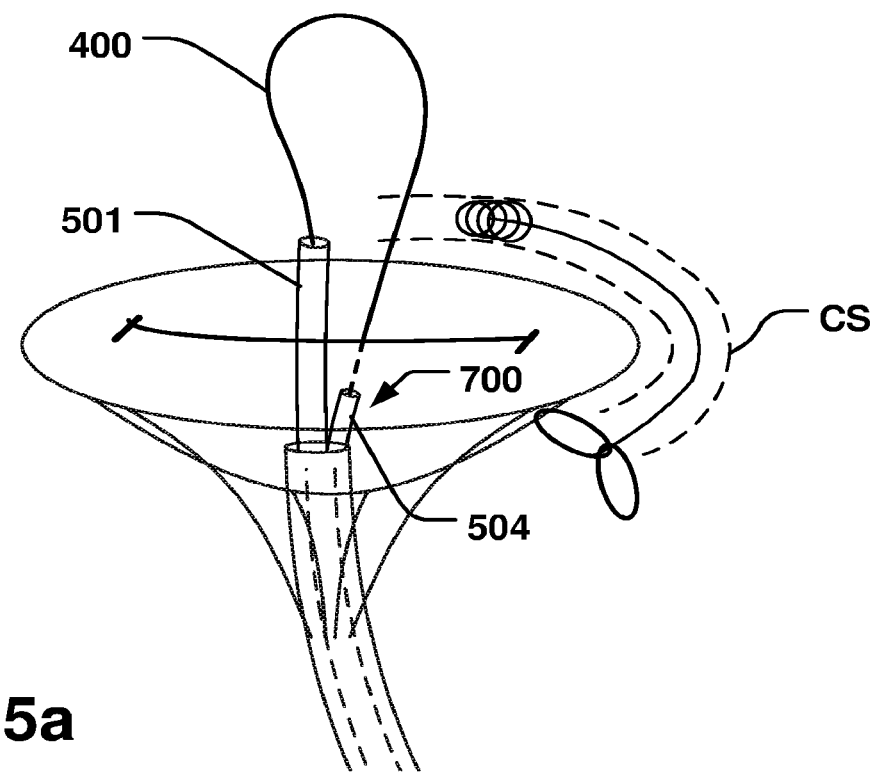
FIG. 5a is a schematic illustration of an arrangement of a delivery device, an annuloplasty implant and a coronary sinus downsizing device in a method according to one example.
Figure 5B:
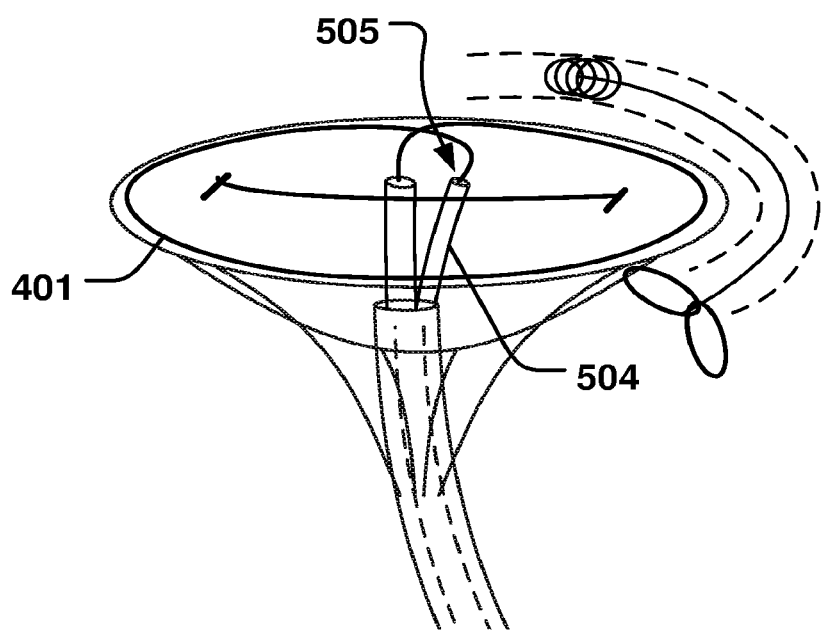
FIG. 5b is a schematic illustration of an arrangement of a delivery device, an annuloplasty implant and a coronary sinus downsizing device in a method according to one example, where the annuloplasty implant has been further ejected from the delivery device.

The stabilizing unit 700 may comprise a second delivery wire 504 that is movable relative the delivery catheter 501 in the longitudinal direction thereof, as illustrated in FIGS. 5a-b. The method 200 may comprise ejecting 220 the annuloplasty implant 400 from the delivery catheter 501 in the atrium of the heart while fixating 221 the position of a portion of the annuloplasty implant being connected to a distal portion 505 of the second delivery wire 504, as schematically illustrated in FIG. 5a. The position if the implant 400 relative to the valve 800 can thus be effectively controlled. The second delivery wire 504 may be moved relative the delivery catheter 501 to arrange the implant 400 as desired relative to the valve 800 during the procedure. It is conceivable that the implant 400 is releasably locked to the second delivery wire 504, so that the implant 400 is released when assuming the correct position. This also provides for controlling the position of the free end of the implant 400 that otherwise may cause trauma to the atrium, or ventricle, when ejected from the delivery catheter 501.

Thus, the method 200 may comprise ejecting and positioning 222 at least a first support ring 401 of the annuloplasty implant around the annulus on the atrial side of the valve while fixating the position of a portion of the first support ring 401 to the distal portion of the second delivery wire 504, as illustrated in FIG. 5b.

The method 200 may comprise positioning 223 the stabilizing unit 700 in the ventricle of the heart, and guiding 224 the annuloplasty implant 400 through an aperture 701 in a distal portion of the stabilizing unit 700, while ejecting 225 the annuloplasty implant 400 from the delivery catheter in the atrium, to guide the annuloplasty implant 400 on the ventricular side of the heart valve, as illustrated in FIG. 6. This may provide for facilitating the positioning of the implant on the ventricular side of the valve since it may be easier to steer the implant to the ventricular side without having to rotate the implant through the commissures. An aperture 701 or any other structure configured to steer the implant 400, such as a wire forming a hook-shape, may be used as a guiding element.

The method 200 may comprise positioning 226 at least a first support ring 401 of the annuloplasty implant around the annulus on the atrial side of the valve while the stabilizing unit guides 227 a second support ring 402 of the annuloplasty implant around the annulus on the ventricular side of the valve. The method thus provides for a facilitated positioning of a helix-shaped implant on either sides of the valve leaflets, as illustrated in FIG. 6.

Temporarily transferring the coronary sinus contractor device (CS device) 100 to an activated state may comprise moving 228 the distal anchoring portion 102 in a longitudinal direction of the CS device to reduce the distance between the distal anchoring portion 102 and the proximal expandable portion 101. As the length of the CS device is reduced between the two anchoring sections, the shape of the CS vessel, and thereby the annulus, is modified, to provide the downsizing effect so that the diseased leaflets can co-apt. The combination of reducing the length CS device and having a proximal expandable portion 101 that efficiently provides a counter force against the tissue wall 804 at the entrance of the CS vessel, may provide for greatly improving the downsizing effect. Since the proximal expandable portion 101 may be shaped and adapted for positioning against the tissue wall 804 at the entrance of the CS, and not inside the CS itself it also reduces the risk of damaging the CS. Also, since the proximal expandable portion 101 may be positioned outside the CS it is not constrained by the size of the CS and can thus be reversibly expanded to a diameter that spreads the force over a larger portion, thus reducing the pressure on the tissue. This also reduces risk of damages.

Figure 4D:
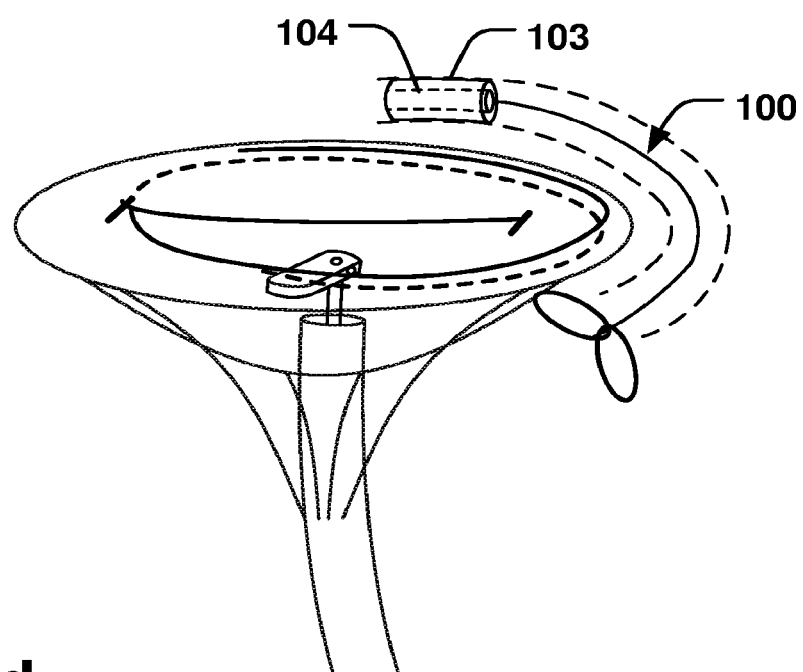
FIG. 4d is a schematic illustration of an arrangement of a delivery device, an annuloplasty implant and a coronary sinus downsizing device in a method according to one example, where the annuloplasty implant has been positioned on the ventricular- and atrial sides of the heart valve.

As schematically illustrated in FIG. 4d, the distal anchoring portion 102 may comprise a balloon 103 having a lumen 104 in the longitudinal direction of the CS device, which corresponds to the longitudinal direction of the CS vessel. The method 200 may comprise inflating 229 the balloon 103 to secure the position of the balloon 103 in a distal portion of the CS, and providing 230 fluid communication between the distal region of the CS and a proximal region thereof. Thus, it is possible to let blood flow through the balloon 103, which improve the safety of the procedure, while achieving an anchoring effect in the CS vessel.

The present invention has been described above with reference to specific embodiments. However, other embodiments than the above described are equally possible within the scope of the invention. The different features and steps of the invention may be combined in other combinations than those described. The scope of the invention is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

The invention claimed is:

1. A kit comprising an implant delivery catheter for repairing a defective heart valve and an annuloplasty implant, wherein the implant delivery catheter comprises: a first part configured to be arranged on a ventricular side of the heart valve, wherein the first part is configured to form a first curve around chordae of the heart valve on the ventricular side and a second part configured to be arranged on an atrial side of the heart valve, wherein the second part is configured to form a second curve along an annulus of the heart valve on the atrial side so that the first curve and the second curve form a helix shape with two continuously connected loops, on opposite sides of the heart valve, being connected through a commissure of the heart valve; wherein the annuloplasty implant is configured to be arranged in the delivery catheter and to be ejected from the delivery catheter while retracting the delivery catheter such that the implant is arranged along the first and second curve on the ventricular and atrial side when retracting the delivery catheter; wherein the annuloplasty implant has a predefined ring-shape having a curvature corresponding substantially to the first and second curve such that, when ejected from the delivery catheter, the annuloplasty implant is arranged along the first and second curve; and wherein the predefined ring-shape is a helix-shaped ring, whereby a first support ring of the helix-shaped ring is positioned on the atrial side and a second support ring of the helix-shaped ring is positioned on the opposite ventricular side when ejected from the delivery catheter, whereby leaflets of the heart valve are pinched between the first and second support rings.

2. The kit according to claim 1, wherein the implant delivery catheter is configured to be inserted through the commissure of the heart valve.

3. The kit according to claim 1, wherein the first and second curve of the implant delivery catheter is configured to be aligned in the plane of the heart valve, such that the annuloplasty implant is positioned generally in said plane when retracting the delivery catheter.

4. The kit according to claim 1, wherein the annuloplasty implant is configured to retain a modified shape of the annulus.

5. The kit according to claim 1, wherein the annuloplasty implant is configured to be decoupled from the delivery catheter.

6. The kit according to claim 1, wherein the annuloplasty implant is configured to assume an elongated configuration when confined in the delivery catheter and to assume the predefined shape when ejected from the delivery catheter.

7. The kit according to claim 1, wherein the shape of the first curve is different from the shape of second curve when positioned on the opposite sides of the heart valve.

* * * * *